United States Patent [19]

Greter

[11] Patent Number: 5,081,872
[45] Date of Patent: Jan. 21, 1992

[54] PIPETTING INSERT

[75] Inventor: Andreas Greter, Steinhausen, Switzerland

[73] Assignee: Hoffman-La Roche Inc., Nutley, N.J.

[21] Appl. No.: 526,347

[22] Filed: May 21, 1990

[30] Foreign Application Priority Data

Jun. 1, 1989 [CH] Switzerland .................... 2052/89

[51] Int. Cl.⁵ ............................ G01N 1/10; B01L 3/02
[52] U.S. Cl. ............................ 73/864.74; 73/863.85; 73/864.01
[58] Field of Search ........... 73/863.85, 864.74, 864.01, 73/864.14, 864.86

[56] References Cited

U.S. PATENT DOCUMENTS

| | | | |
|---|---|---|---|
| 3,608,550 | 9/1971 | Stawaki | 604/414 |
| 3,783,694 | 1/1974 | Otte et al. | 73/864.74 |
| 3,870,183 | 3/1975 | Luczkiw | 215/247 |
| 4,134,512 | 1/1979 | Nugent | 215/247 |
| 4,543,101 | 9/1985 | Crouch | 604/411 |
| 4,808,381 | 2/1989 | McGregor et al. | 422/100 |
| 4,879,915 | 11/1989 | Spencer | 73/864.74 |
| 4,892,710 | 1/1990 | Wong et al. | 73/864.74 X |
| 4,939,940 | 7/1990 | Tsukida | 73/864.74 |
| 4,951,512 | 8/1990 | Mazza et al. | 73/864.74 X |
| 4,976,925 | 12/1990 | Porcher et al. | 73/864.74 X |
| 4,982,740 | 1/1991 | Broden | 128/760 |

FOREIGN PATENT DOCUMENTS

516430 6/1981 Australia .
2824588 12/1978 Fed. Rep. of Germany .
WO84/04673 12/1984 PCT Int'l Appl. .

Primary Examiner—Tom Noland
Attorney, Agent, or Firm—George M. Gould; George W. Johnston; Stephen L. Malaska

[57] ABSTRACT

A pipetting insert for a pipetting device for taking a liquid sample from a vacuum tube closed in air-tight manner by a stopper. In order to prevent the undesirable escape of fragments of a sample from the vacuum tube before the sample is taken, the pipetting insert is made of plastic, has an elongated body which has a conical part at one end, a hollow tip in the form of a wall for piercing by a pipetting needle at the other end, and a central tubular part therebetween. The central part of the body has a bore along its longitudinal axis for connecting the interior of the conical part to the interior of the hollow tip, and the outer wall of the central part of the body contains at least one connecting duct which extends between the conical part and the tip and the cross-section of which is considerably smaller than the cross-section of the bore in the central part of the body.

14 Claims, 7 Drawing Sheets

PIPETTING INSERT

FIELD OF THE INVENTION

A pipetting insert for a pipetting device for taking a liquid sample from a vacuum tube closed in airtight manner by a stopper.

BACKGROUND OF THE INVENTION

Vacuum tubes ("vacutainers") are presently the most commonly-used sample tubes. A blood sample is usually taken by means of a cannula pointed at both ends, one tip being inserted into a patient's vein whereas the other tip is inserted into an evacuated vacuum tube through the stopper thereof. When the connection has been made, the difference in pressure causes the blood sample to flow into the vacuum tube.

After the sample has been taken, the vacuum tube usually remains at negative pressure. If the stopper is removed in the laboratory in order to take the sample out of the vacuum tube, the sudden equalization in pressure may result in an air stream entering the tube, so that fragments of sample are sprayed out. There will thus be a serious risk of infection, because the samples (e.g. blood samples) in vacuum tubes are normally considered as possibly infectious. Laboratory staff handling these samples run the risk of being infected by any disease transmitted by a sample. It is therefore very important to reduce the handling of samples to a minimum and to eliminate dangerous manipulations.

This problem was addressed in the prior art by means of a pipetting insert (PCT patent application, publication number WO 87/05208) which contains a pipetting duct ending in a tip for piercing the stopper of the vacuum tube when the pipetting insert is placed thereon. The pipetting duct has two functions. On the one hand it equalizes the pressure, so that after the pipetting insert has been fitted, the pressure in the tube is equal to the air pressure. On the other hand the pipetting duct serves as a guide element for the suction tube or needle of a pipetting device for taking the sample out of the tube.

However, when the pipetting insert known in the art is inserted through the stopper of the vacuum tube there is a sudden equalization of pressure, so that if the pressure difference is relatively large, fragments of sample are sprayed out of the tube, with the aforementioned risk of infection.

Additionally, as soon as the known pipetting insert has been inserted through the stopper of the vacuum tube, the pipetting duct connects the interior of the tube to the environment, i.e. a sample-containing tube is open. There is therefore a risk that when the tube is handled, fragments of sample will escape from the tube and cause a risk of infection. Also, a part of the sample may be lost by evaporation.

SUMMARY OF THE INVENTION

The object of the invention therefore is to devise a pipetting insert which does not have the above described disadvantages.

According to the invention, these problems are solved by a pipetting insert having a housing with an inner and an outer wall of substantially the same length and the housing is open on one end but closed on its other end. The inner wall defines a bore extending from the open end of the housing to the closed end and the bore has a diameter which is substantially perpendicular to a longitutinal axis of the housing. The housing further has a central tubular part connected to a conical part on one end and connected to a tip means on its second end. The conical part is open on both of its ends. The tip means is formed by the inner and the outer walls at the closed end of the housing. In the outer wall of the housing is a connecting duct means open on both of its ends and extending from the tip means in a direction toward the conical part. The diameter of the connecting duct is substantially smaller than the diameter of the bore of the housing and is used to equalize pressure in the vacuum tube with the pressure of the atmosphere surrounding the tube while at the same time preventing loss of the sample from the tube. The novel insert is preferably made of plastic.

The pipetting insert according to the invention has the following particular advantages:

Owing to the relatively small cross-section of the at least one connecting duct, there is a relatively slow equalization of pressure after the pipetting insert has been fitted on to the vacuum tube. It is therefore impossible for fragments of sample to escape from the tube during the pressure equalization process.

The piercable wall of the tip of the pipetting insert is pierced only at the time when the sample has been taken out of the tube by the needle of a pipetting device. Until then, the tube remains closed by the stopper and the pipetting insert inserted therein, so that it is quite impossible for the sample to escape from the tube. There is therefore no possible loss of sample through evaporation or manipulation of the tube.

In order to remove the sample from the tube, after the pipetting insert has been inserted and the pressure has been equalized, a pipetting needle is introduced through the bore in the central part of the pipetting insert and pierces the wall at the tip of the pipetting insert. It is thus impossible for a fragment of sample to enter the bore and stick to the outer wall of the pipetting needle. There is thus no risk of undesirable "carry-over" of fragments of samples to the outer wall of the needle.

The aforementioned advantages result in maximum protection of laboratory staff against the risk of infection.

The pipetting insert according to the invention is also suitable for manufacture as a cheap throwaway part.

BRIEF DESCRIPTION OF THE DRAWINGS

Embodiments of the invention will now be described with reference to the accompanying drawings, in which.

DETAILED DESCRIPTION OF THE PREFERRED EMBODIMENTS

Figure 1:
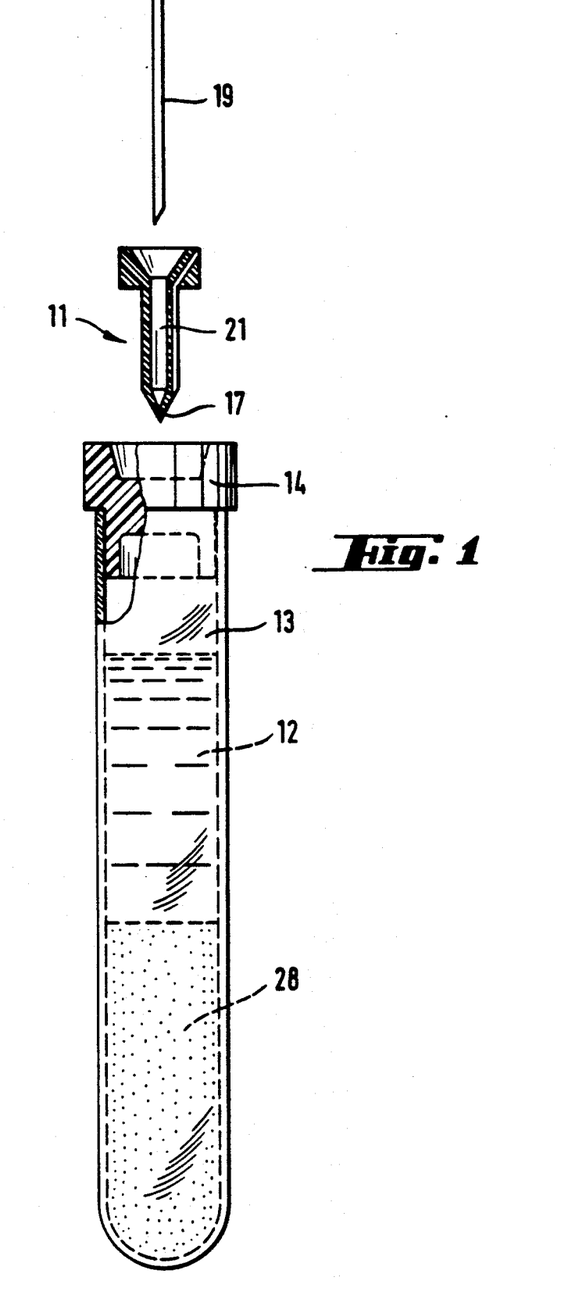
FIG. 1 is an exploded view of a vacuum tube 13, a pipetting insert 11 according to the invention and a pipetting needle 19.

As FIG. 1 shows, a pipetting insert 11 according to the invention is used as a connecting member between a needle 19 of a pipetting device (not shown in FIG. 1) and a vacuum tube 13 which e.g. contains a blood sample and is closed in an airtight manner by a stopper 14 which does not contain any opening. The blood sample consists e.g. of a liquid part 12 and a solid part 28, separated from one another by centrifuging. In order to take a given quantity of the liquid sample 12, the pipetting insert 11 is first introduced through stopper 14, using a suitable device not shown in FIG. 1, until its tip is in the interior of vacuum tube 13. Needle 19 is then inserted into the vacuum tube 13 through a bore 21 in the pipetting insert 11, the wall at the tip of the vacuum insert being pierced by the needle 19.

The pipetting insert 11 is preferably made by injection-moulding from a suitable plastics. The plastics must be hard enough for the pipetting insert 11 to remain intact when piercing the stopper 14, but must be soft enough for the tip 17 of the insert to be easy to pierce with a conventional pipetting needle 19. One example of a plastics suitable for manufacturing the pipetting insert 11 is polyethylene, more particularly high-density polyethylene (HDPE), which is also called low-pressure polyethylene (NDPE) or hard polyethylene.

Figure 2:
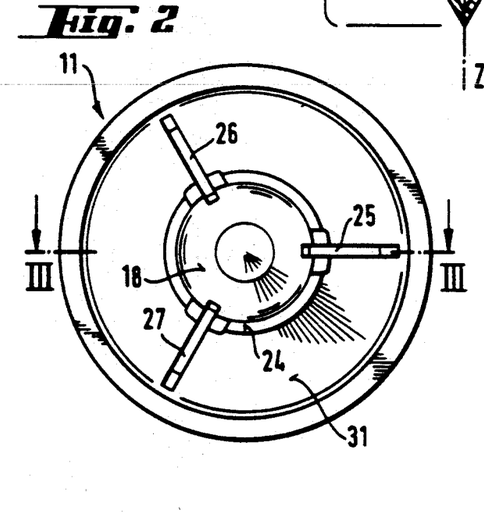
FIG. 2 is a bottom view of a first embodiment of a pipetting insert 11 according to the invention.
Figure 3:
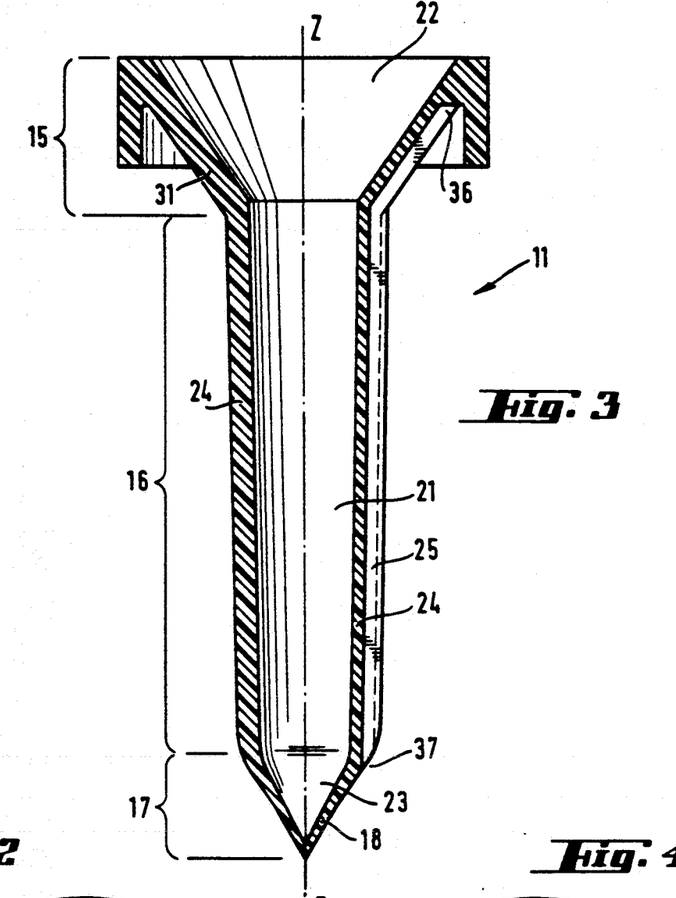
FIG. 3 is a longitudinal section of the embodiment in FIG. 2 along line III—III.
Figure 4:
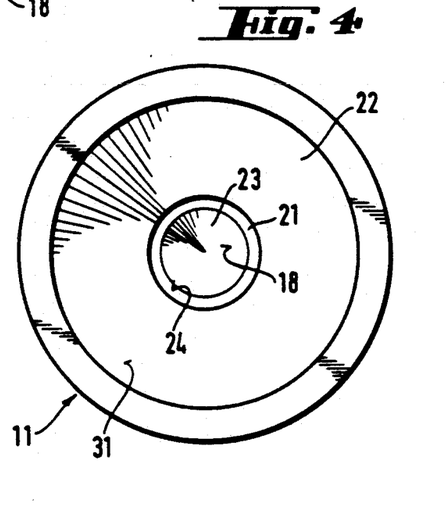
FIG. 4 is a plan view of the embodiment of FIGS. 2 and 3.

A first embodiment of a pipetting insert 11 according to the invention will now be described with reference to FIGS. 2-4. FIG. 2 is a view of the embodiment from beneath. FIG. 3 shows a longitudinal section through the embodiment along line III—III in FIG. 2, and FIG. 4 is a plan view of the embodiment.

As FIG. 3 shows, the pipetting insert 11 has an elongated body having a conical part 15 at one end and a hollow tip 17 at the other end. Tip 17 is formed by a conical wall 18 which can be pierced by a pipetting needle. The elongated body of the pipetting insert 11 has a central tubular part 16 which extends between the conical part 15 and the tip 17.

The central part 16 of the pipetting insert 11 has a bore 21 which extends along the longitudinal axis Z—Z and connects the interior 22 of the conical part 15 to the interior 23 of the hollow tip 17. The central part 16 of the pipetting insert has an outer wall 24 containing at least one connecting duct 25 which extends substantially between the conical part 15 and the tip 17 and the cross-section of the bore 21. The connecting duct 25 has an upper end 36 and a lower end 37. The pipetting insert 11 preferably has at least two such connecting ducts, symmetrically disposed around the longitudinal axis Z—Z of the pipetting insert. The embodiment in FIGS. 2-4 has three connecting ducts 25, 26, 27 symmetrically disposed around the longitudinal axis Z—Z of the pipetting insert.

As FIGS. 2 and 3 show, each duct is in the form of a groove in the outer wall 24 and in the outer wall of the conical part 15. Along the central part 16 of the pipetting insert, the grooves preferably extend substantially parallel to the longitudinal axis Z—Z of the pipetting insert.

As described in detail hereinafter, the connecting ducts 25, 26, 27 are for equalizing the pressure between the interior of the sealed vacuum tube 13 and the air outside the tube. The cross-section of the connecting ducts 25, 26, 27 is made so small that when the pressure is being equalized the sample cannot escape from the tube through the ducts.

Figures 13, 14:
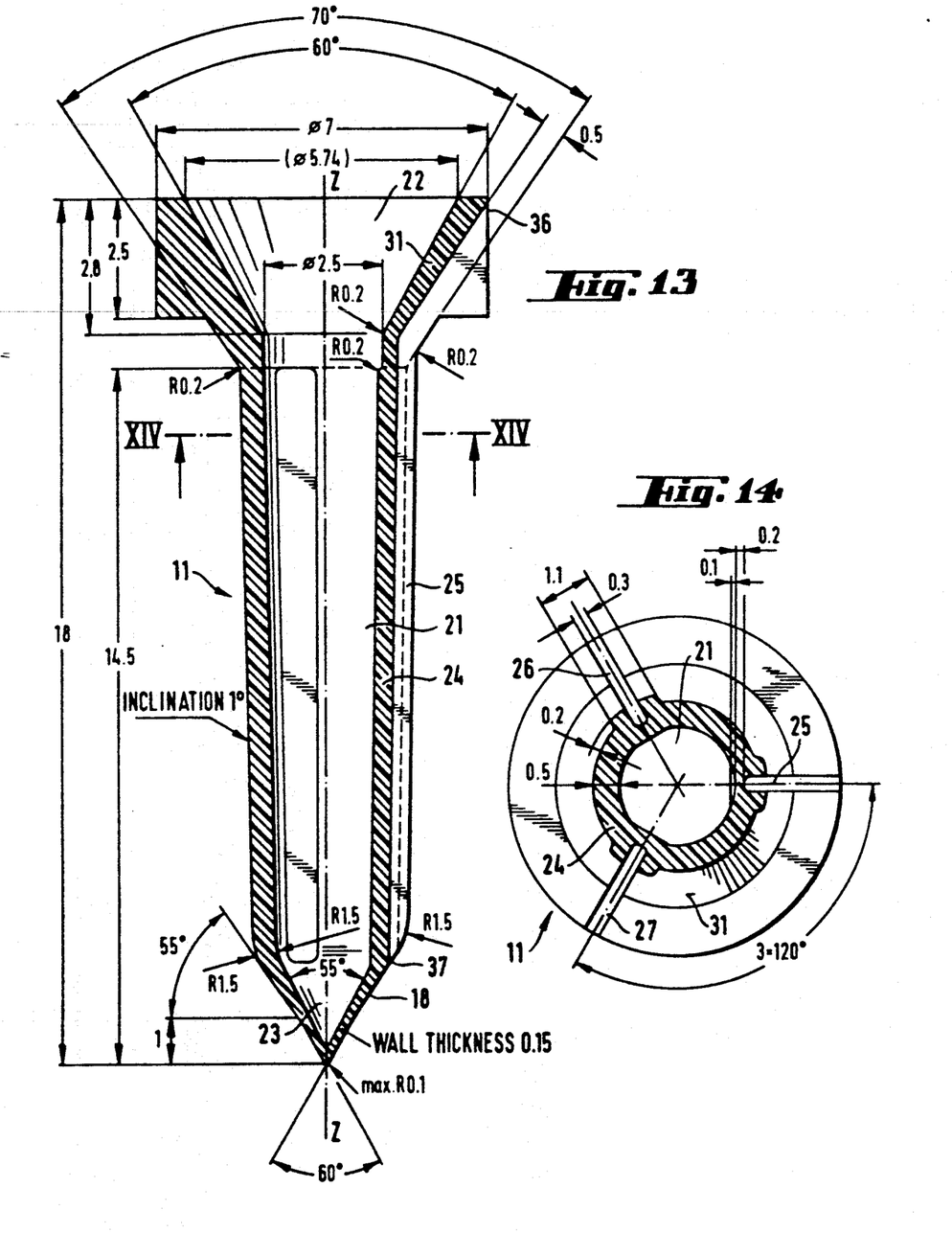
FIG. 13 is a longitudinal section of the embodiment in FIG. 12, showing dimensions of the pipetting insert in millimeters.
FIG. 14 shows the cross-section XIV—XIV in FIG. 13, giving the dimensions of the pipetting insert 11 in millimeters.

The thickness of the wall 18 of the tip 17 of the pipetting insert is made small enough for it to be easily pierced by a conventional pipetting needle. As shown in FIG. 13 the thickness of this wall is about 0.15 mm.

Figure 5:
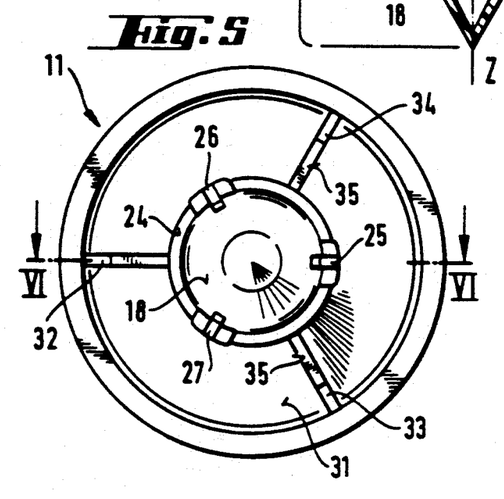
FIG. 5 is a bottom view of a second embodiment of a pipetting insert 11 according to the invention.
Figure 6:
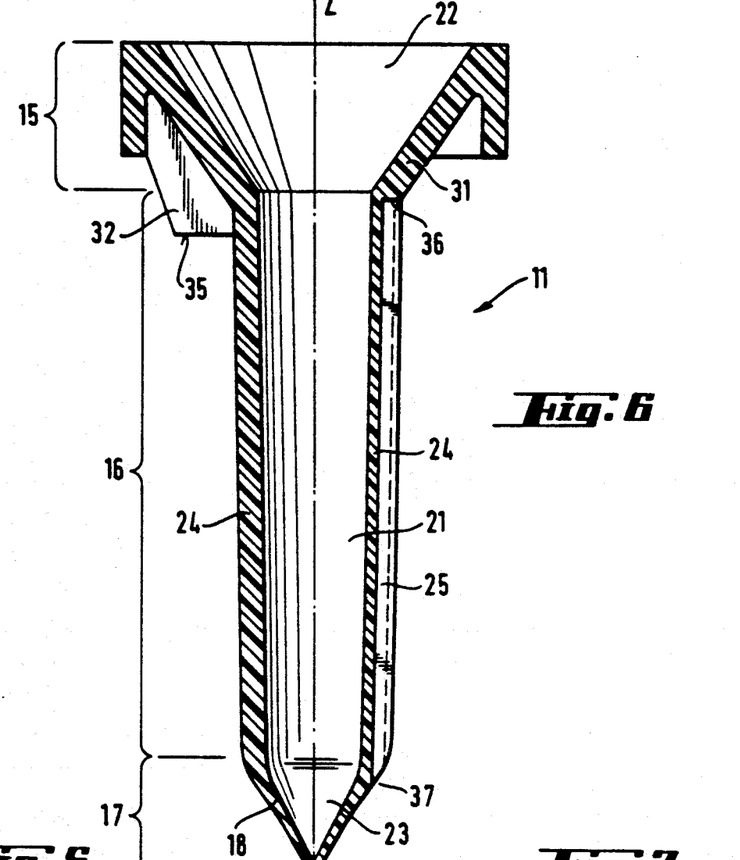
FIG. 6 is a longitudinal section through the embodiment in FIG. 5 along line VI—VI.
Figure 7:
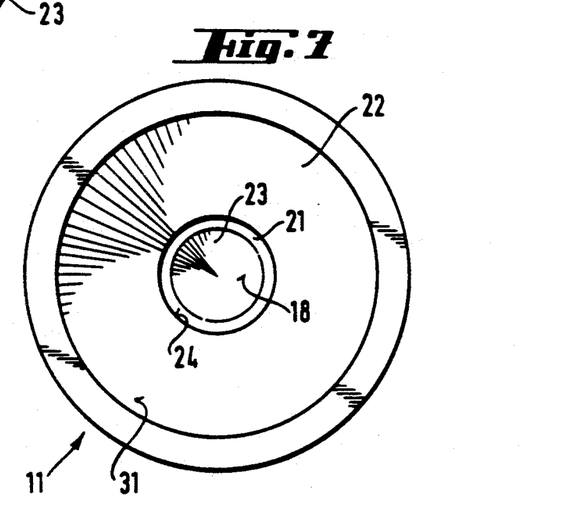
FIG. 7 is a plan view of the embodiment of FIGS. 5 and 6.

A second embodiment of a pipetting insert 11 according to the invention will now be described with reference to FIGS. 5-7. FIG. 5 is a view of the second embodiment from underneath. FIG. 6 shows a longitudinal section of the embodiment through line VI—VI in FIG. 5. FIG. 7 is a plan view of the embodiment.

The second embodiment in FIGS. 5-7 is substantially identical with the embodiment in FIGS. 2-4, so that the preceding description of FIGS. 2-4 largely applies also to FIGS. 5-7.

The second embodiment in FIGS. 5-7 differs from the embodiment in FIGS. 2-4 in only the following features:

In the second embodiment the connecting ducts 25, 26, 27 extend only over the entire length of the central part 16 of the pipetting insert. The ducts are therefore somewhat shorter than in the first embodiment in FIGS. 2-4.

In the second embodiment the outer wall of the conical part 15 of the pipetting insert has at least one fin-like projection 32 which extends along the longitudinal axis Z—Z of the body and has an end 35 facing the tip 17. End 35 is nearer tip 17 than the upper end 36 of the at least one connecting duct 25, upper end 36 being adjacent the conical part 15 or disposed at the boundary between the central part 16 and the conical part 15.

In a preferred embodiment the outer wall 31 of the conical part 15 has at least two of the previously-described projections. As FIG. 5 shows, the outer wall 31 of the conical part 15 has three fin-like projections 32, 33, 34, disposed symmetrically around the longitudinal axis Z—Z of the pipetting insert.

Projections 32-34 and ducts 25-27 are positioned relatively to one another so as to ensure that the intended equalization of pressure can occur through the connecting ducts 25-27.

A typical use of the pipetting insert 11 according to the invention will now be described with reference to FIG. 1 and 8-11. FIGS. 8-11 inter alia show a pipetting insert according to FIGS. 5-7, but the following description applies equally to the embodiment of the pipetting insert in FIGS. 2-4.

In order to take a given quantity of a sample 12 from a vacuum tube 13, a pipetting insert 11 according to the invention and a needle 19 of a pipetting device are used as in the arrangement diagrammatically shown in FIG. 1.

Figure 8:
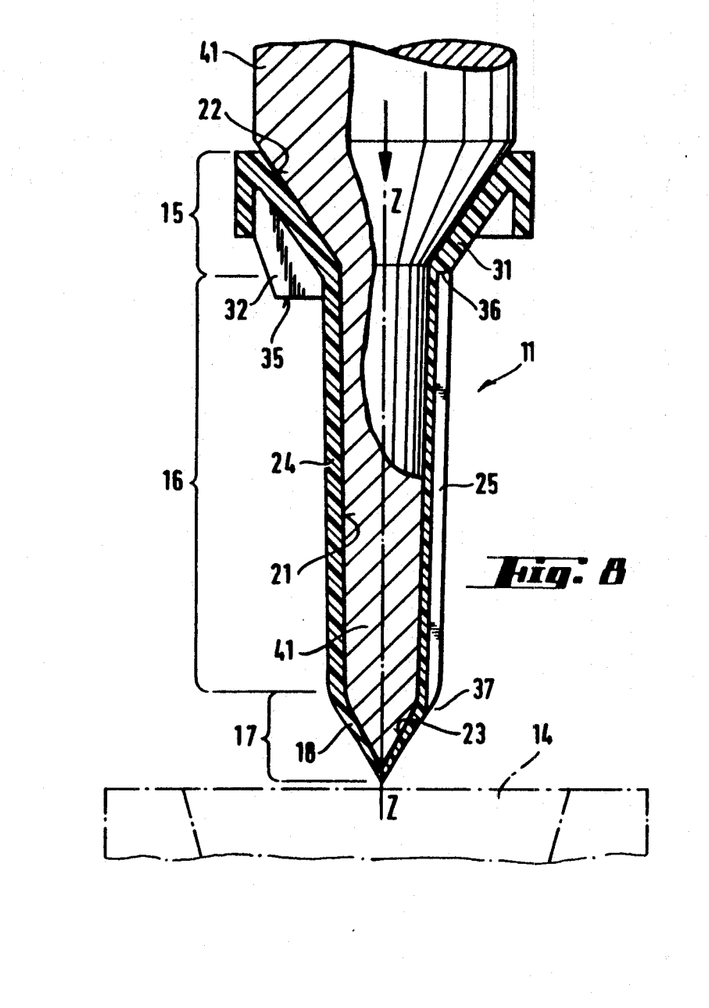
FIG. 8 is a diagrammatic longitudinal section of the pipetting insert 11 of FIGS. 5-7, illustrating a pressure spike 41; introduced in the pipetting insert.
Figure 9:
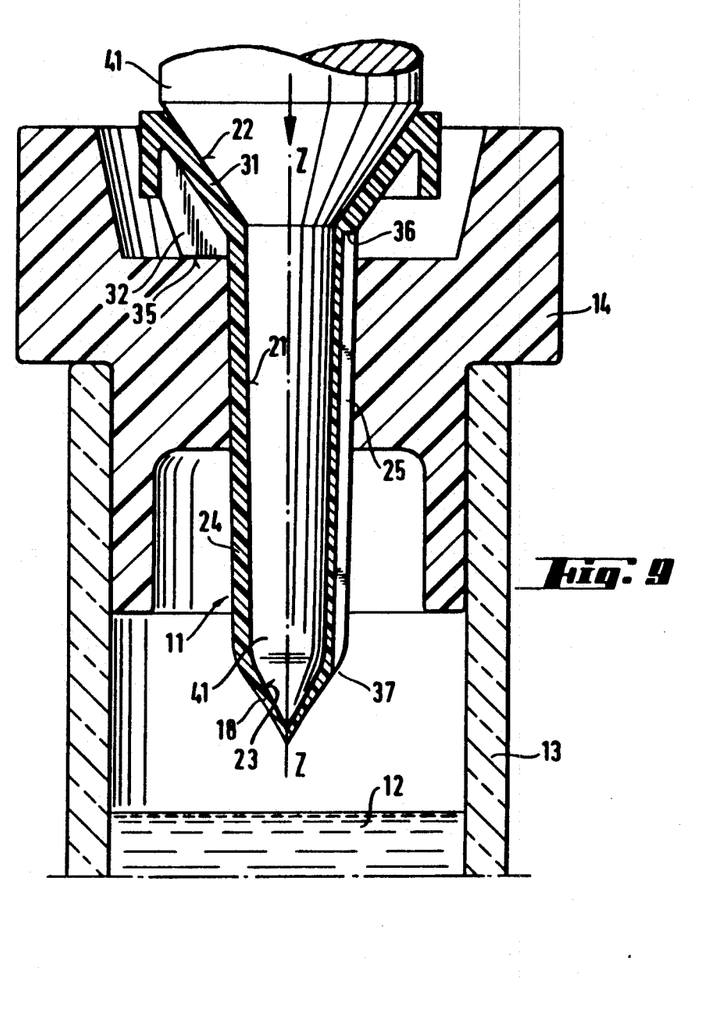
FIG. 9 is a diagrammatic longitudinal section illustrating the embodiment of the pipetting insert 11 of FIGS. 5-7 through the stopper 14 of a vacuum tube 13, using the pressure spike 41.

As shown in FIGS. 8 and 9, a pipetting insert 11 is introduced through the stopper 14 of the vacuum tube 13 by a suitable device, in a step in preparation for the subsequent sample-taking. For this purpose, as shown in FIG. 8, a pressure spike 14 is first inserted into the bore 21 of the pipetting insert 11. As FIG. 8 shows, the shape of the pressure spike 41 is preferably adapted very accurately to the inner wall of the upper conical part of the pipetting insert 11, the inner wall of the bore and the hollow tip inside the pipetting insert 11. Before the pipetting insert 11 is introduced through the stopper 14 of the vacuum tube 13, the pressure spike 41 is introduced into the pipetting insert until it occupies the position shown in FIG. 8.

In order to introduce the pipetting insert 11 into the stopper 14, the pipetting insert 11 is pressed by the pressure spike 41 against the central part of the stopper 14 in the direction indicated by an arrow, until the pipetting insert 11 pierces the stopper 14 and takes up the position shown in FIG. 9. As FIG. 9 shows (and this also applies to the projections 33-34 not shown in FIG. 9), the projection 32 serves as a spacer which ensures that the at least one connecting duct 25 connects the interior of the vacuum tube 13 to the air outside the tube and thus enables the pressure to be equalized.

Figures 10, 11:
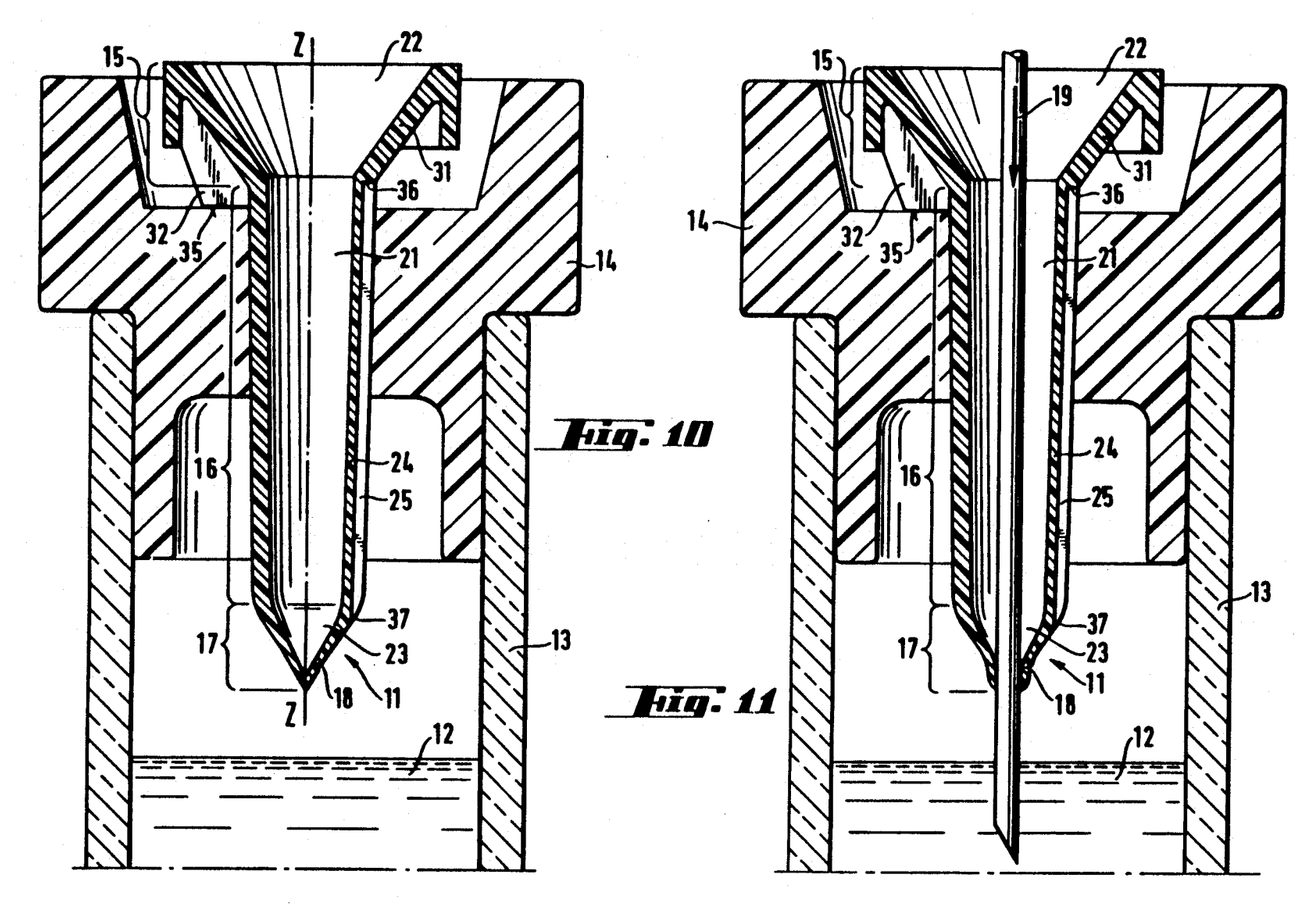
FIG. 10 is a diagrammatic longitudinal section of the pipetting insert 11 inserted as per FIG. 9, after removing the spike 41.
FIG. 11 is a diagrammatic longitudinal section of the pipetting insert 11 inserted as per FIG. 9, illustrating the tip 17 of the pipetting insert 11 pierced by a pipetting needle 19 for removing a sample from the vacuum tube.

After the pipetting insert 11 has been introduced into the stopper 14 in the manner described, the pipetting insert 11 remains in the stopper 14 in the position shown in FIG. 10. Note that the conical wall 18 of the tip 17 of the pipetting insert 11 remains intact after insertion into the plug 14, and prevents the sample from escaping from the vacuum tube 13 through the bore 21.

Vacuum tubes 13 containing samples and equipped with a pipetting insert 11 in the position shown in FIG. 10, are sealed containers. They can therefore be used for a wide variety of process steps, such as centrifuging or agitation of vacuum tubes, without risk of fragments of sample escaping from the vacuum tubes.

As diagrammactically shown in FIG. 11, in order to take a given quantity of sample 12 from vacuum tube 13, a pipetting needle 19 is introduced through the bore 21 of the pipetting insert 11 in the direction indicated by an arrow, until it occupies the position shown in FIG. 11. During the insertion process, the wall 18 of the tip 17 of the pipetting insert 11 is pierced by the needle 19. After removal of the sample, the needle 19 is taken out of the vacuum tube 13 or the pipetting insert 11. The slit left in wall 18 by the perforation is very small, so that if the vacuum tube is handled normally, it is very unlikely that samples of fragments will escape from the vacuum tube.

Figure 12:
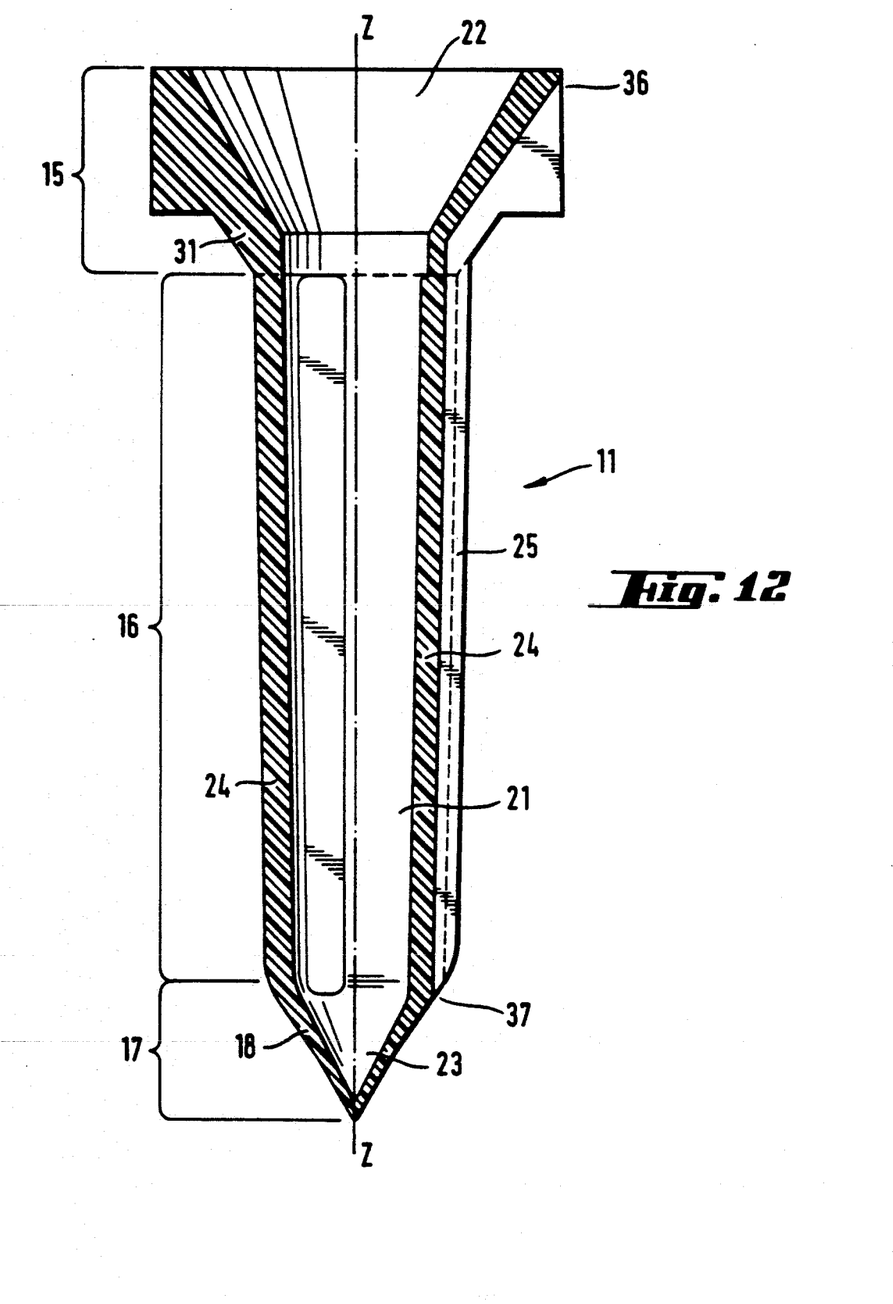
FIG. 12 is a longitudinal section through a third embodiment of the pipetting insert of FIGS. 2-4 according to the invention.

FIG. 12 shows a longitudinal section of a variant of the embodiment in FIGS. 2-4. In this variant the connecting ducts 25, 26, 27 extend to the top edge of the conical part 15 of the pipetting insert.

The dimensions in the embodiment in FIG. 12 are given in millimetres in FIGS. 13 and 14. FIG. 13 shows a cross-section along the longitudinal axis of the pipetting insert. FIG. 14 shows cross-section XIV—XIV of FIG. 13.

The dimensions given in FIGS. 13 and 14 largely apply also to the embodiments in FIGS. 2-4 and 5-7.

Within the scope of the invention some of the dimensions of the pipetting insert should be chosen within the ranges indicated hereinafter:

The thickness of the wall 24 of the central tubular part 16 of the insert 11 should preferably be chosen in a range between about 0.3 mm and about 1.0 mm.

The thickness of the thinnest part of the wall 18 of the tip 17 of the insert 11 should preferably be chosen in a range between about 0.1 mm and about 0.3 mm.

The average diameter of the bore 21 of the central part 16 of the insert 11 should preferably be chosen in a range between about 1.5 mm and about 4.0 mm.

The diameter of each of the connecting ducts 25, 26, 27 along the outer wall 24 of the insert 11 should preferably be chosen in a range between about 0.1 mm and about 0.5 mm.

I claim:

1. A pipetting insert for a pipetting device for taking a sample from a vacuum tube closed in an airtight manner by a stopper comprising:

a housing having an outer wall and an inner wall of substantially the same length forming a central tubular part connected to a conical part and to tip means, the housing having an open end and a closed end, the inner wall defining a bore extending from the open end of the housing to the closed end of the housing and the bore having a diameter substantially perpendicular to a longitudinal axis of the housing, the central tubular part having a first end connected to the conical part, which is open on both of its ends, and the central tubular part having a second end connected to the tip means, said tip means being formed by the inner and the outer walls at the closed end of the housing, and used for piercing the stopper of the vacuum tube and for being pierced by the pipetting device, and the outer wall defining at least one connecting duct means being open on both ends and having a diameter substantially smaller than the diameter of the bore, said connecting duct means extending from the tip means in a direction toward the conical part and used for equalizing pressure in the vacuum tube with atmospheric pressure surrounding the tube while at the same time preventing loss of the sample from the vacuum tube.

2. The pipetting insert according to claim 1 wherein the tip means comprises: a hollow tip having a conical shaped tip end in a direction away from the conical part, the tip end formed by the inner and outer walls.

3. The pipetting insert according to claim 2 wherein the outer wall of the hollow tip has a thickness in a range between about 0.1 mm and about 0.3 mm.

4. The pipetting insert according to claim 1 wherein the conical part comprises: at least one projection means extending from the conical part along the outer wall of the housing in a direction toward the tip means to a point closer to the tip means than the open end of the connecting duct means closest to the conical part.

5. The pipetting insert according to claim 4 wherein the projection means comprises: at least two projections symmetrically disposed around the longitudinal axis of the housing.

6. The pipetting insert according to claim 1 wherein the connecting duct means comprises: at least two connecting ducts symmetrically disposed around the longitudinal axis of the bore of the housing.

7. The pipetting insert according to claim 1 wherein the connecting duct means is in the form of a groove in the outer wall which extends in a direction substantially parallel to the longitudinal axis of the central tubular part.

8. The pipetting insert according to claim 1 wherein the connecting duct means extends from the tip means to the open end of the housing.

9. The pipetting insert according to claim 1 wherein the connecting duct means extends from the tip means to a point in the outer wall of the conical part.

10. The pipetting insert according to claim 1 wherein the connecting duct means extends from the tip means to the conical part.

11. The pipetting insert according to claim 1 wherein the insert is made of plastic.

12. The pipetting insert according to claim 1 wherein the outer wall of the central tubular part has a thickness in a range of between about 0.3 mm and about 1.0 mm.

13. The pipetting insert according to claim 1 wherein the diameter of the bore of the central tubular part is in a range between about 1.5 mm and about 4.0 mm.

14. The pipetting insert according to claim 1 wherein the diameter of each of the connecting duct means along the outer wall of the housing is in a range between about 0.1 mm and about 0.5 mm.

* * * * *